(12) United States Patent
Suzuki

(10) Patent No.: US 7,060,914 B2
(45) Date of Patent: Jun. 13, 2006

(54) BIOELECTRICAL IMPEDANCE MEASURING DEVICE

(75) Inventor: Shun Suzuki, Tokyo (JP)

(73) Assignee: Tanita Corporation, Tokyo (JP)

( * ) Notice: Subject to any disclaimer, the term of this patent is extended or adjusted under 35 U.S.C. 154(b) by 56 days.

(21) Appl. No.: 10/862,453

(22) Filed: Jun. 8, 2004

(65) Prior Publication Data

US 2004/0251057 A1      Dec. 16, 2004

(30) Foreign Application Priority Data

Jun. 16, 2003    (JP)     ............................. 2003-170434

(51) Int. Cl.
   *G01G 21/28*     (2006.01)
   *A61B 5/05*      (2006.01)
(52) U.S. Cl. ........................ 177/238; 600/547; 174/54
(58) Field of Classification Search ................ 600/547; 177/238–241; 174/54
   See application file for complete search history.

(56) References Cited

U.S. PATENT DOCUMENTS

| | | | | | |
|---|---|---|---|---|---|
| 5,579,782 | A | * | 12/1996 | Masuo | ........................ 600/547 |
| 5,817,031 | A | * | 10/1998 | Masuo et al. | ................ 600/547 |
| 6,088,615 | A | * | 7/2000 | Masuo | ........................ 600/547 |
| 6,308,096 | B1 | * | 10/2001 | Masuo | ........................ 600/547 |
| 6,321,112 | B1 | * | 11/2001 | Masuo | ........................ 600/547 |
| 6,369,337 | B1 | * | 4/2002 | Machiyama et al. | ..... 177/25.13 |
| 6,473,642 | B1 | * | 10/2002 | Inoue et al. | ................. 600/547 |
| 6,590,166 | B1 | * | 7/2003 | Yoshida | ................... 177/25.13 |
| 6,718,200 | B1 | * | 4/2004 | Marmaropoulos et al. | .. 600/547 |
| 6,850,798 | B1 | * | 2/2005 | Morgan et al. | ............. 600/547 |
| 2004/0122500 | A1 | * | 6/2004 | Rouns | |

FOREIGN PATENT DOCUMENTS

| | | | | |
|---|---|---|---|---|
| JP | 04-348232 A | * | 12/1992 | ................. 177/238 |
| JP | 05-49050 | | 7/1993 | |
| JP | P3098735 | | 8/2000 | |
| JP | 1095614 A1 | * | 5/2001 | |

* cited by examiner

*Primary Examiner*—Randy W. Gibson
(74) *Attorney, Agent, or Firm*—McDermott Will & Emery LLP

(57) ABSTRACT

A bioelectrical impedance measuring device comprises a first electrode unit and a second electrode unit which are nearly rectangular in shape and have electrodes for measuring a bioelectrical impedance on the top surfaces thereof, and a control circuit unit which incorporates an electric control circuit for measuring a bioelectrical impedance and is detachably attached to the first electrode unit and the second electrode unit via connection terminals. Accordingly, a user can disassemble the device into the control circuit unit, the first electrode unit and the second electrode unit and stack these units and can therefore carry around or store the device easily.

5 Claims, 6 Drawing Sheets

BIOELECTRICAL IMPEDANCE MEASURING DEVICE

BACKGROUND OF THE INVENTION (i) Field of the Invention

The present invention relates to a bioelectrical impedance measuring device which measures a bioelectrical impedance between the bottoms of both feet of a user.

(ii) Description of the Related Art

Bioelectrical impedance measuring devices are known which measure a bioelectrical impedance between the bottoms of both feet of a user and calculate data related to body composition such as a body fat percentage (mass). For example, in a bioelectrical impedance measuring device disclosed in Patent Publication 1, a group of electrodes for both feet, an input unit used by a user to enter personal data such as a body height and a display unit for displaying a calculated body fat percentage (mass) and the like are provided on the top surface of a main body which is capable of measuring a body weight (i.e., a bathroom scale). When a user stands on the main body with the bottoms of both feet in contact with these electrodes, the body weight and bioelectrical impedance of the user are measured, and a body fat percentage (mass) and the like are calculated from these measured values and personal data.

Further, Patent Publication 2 discloses a bioelectrical impedance measuring device similar to the bioelectrical impedance measuring device disclosed in the above Patent Publication 1. In the bioelectrical impedance measuring device disclosed in Patent Publication 2, an electrode unit having a group of electrodes for the left foot and an electrode unit having a group of electrodes for the right foot are formed independently of a main body which incorporates load sensors for measuring a body weight and an electric control circuit for measuring a bioelectrical impedance, and these two electrode units are connected to the main body by electric cables.

Further, Patent Publication 3 discloses a four-point scale for measuring the body weight of a user, wherein on two parallel beams having a load sensor for measuring a body weight provided on both ends of the beams, a plurality of platform members are placed orthogonally to the beams, and adjacent platform members are linked together by link hinges so that these platform members can be folded in the form of a bamboo blind.

Patent Publication 1
Japanese Patent Publication 5-49050

Patent Publication 2
Japanese Patent No. 3,098,735

Patent Publication 3
Specification of U.S. Pat. No. 6,337,446

In the case of a conventional bioelectrical impedance measuring device as disclosed in the above Patent Publication 1, a user stands on the top surface of its main body. Hence, a reduction in the size thereof is limited, and the device is difficult to carry around and requires a large space for storage.

In a bioelectrical impedance measuring device as disclosed in the above Patent Publication 2, electrode units are formed independently of the main body, but the main body is not yet small enough in size, so that this device is also difficult to carry around and requires a large space for storage.

Under the circumstances, it is conceivable to make a conventional bioelectrical impedance measuring device as disclosed in the above Patent Publication 1 foldable in the form of a bamboo blind just like the foldable scale disclosed in the above Patent Publication 3 so as to facilitate carrying and storing of the device. However, in the case of the bioelectrical impedance measuring device, since a plurality of electrodes disposed on the top surface of the main body are connected to an electric control circuit incorporated in the main body by electric wires, the electric wires must be placed over a plurality of platform members, so that a problem such as breaking of the electric wires may occur at the time of folding.

Therefore, an object of the present invention is to provide a bioelectrical impedance measuring device which can measure a bioelectrical impedance between the bottoms of both feet of a user and is carried around or stored easily without having problems such as breaking of electric wires.

SUMMARY OF THE INVENTION

According to an aspect of the present invention, a bioelectrical impedance measuring device of the present invention comprises a first electrode unit and a second electrode unit which are nearly rectangular in shape and have electrodes for measuring a bioelectrical impedance on the top surfaces thereof, and a control circuit unit which incorporates an electric control circuit for measuring a bioelectrical impedance and is detachably attached to the first electrode unit and the second electrode unit via connection terminals. Accordingly, a user can disassemble the device into the control circuit unit, the first electrode unit and the second electrode unit and stack these units and can therefore carry around or store the device easily.

Further, in the bioelectrical impedance measuring device of the present invention which further comprises an auxiliary unit, it is preferable that one end of the first electrode unit and one end of the second electrode unit be placed on the top surfaces of the ends of the control circuit unit and the other end of the first electrode unit and the other end of the second electrode unit be placed on the top surfaces of the ends of the auxiliary unit so as to detachably assemble the control circuit unit, the first electrode unit, the second electrode unit and the auxiliary unit via connection terminals. Thus, since the device in an assembled state is in the form of hollow square when viewed from above, the assembled device shows good strength and rigidity.

Further, in the bioelectrical impedance measuring device of the present invention, it is preferable that the first electrode unit and the second electrode unit be formed in a nearly concave shape when viewed from a longer side thereof and the control circuit unit and the auxiliary unit be formed in a nearly convex shape when viewed from a longer side thereof. Thereby, the control circuit unit and the auxiliary unit and the first electrode unit and the second electrode unit can be stacked stably by fitting their concave and convex portions with a minimum overall height, thereby further facilitating carrying and storing of the device.

Further, in the bioelectrical impedance measuring device of the present invention, it is preferable that the control circuit unit and the auxiliary unit incorporate load sensors for measuring a body weight. As a result, when a user stands on the top surfaces of the first electrode unit and the second electrode unit of the device in an assembled state, the body weight of the user is passed down to the control circuit unit and the auxiliary unit on which the first electrode unit and the second electrode unit are placed and can be measured by the load sensors.

Further, in the bioelectrical impedance measuring device of the present invention, it is preferable that the control circuit unit further incorporate an input unit used by a user to enter personal data, an arithmetic unit for calculating data related to the body composition of the user based on at least the personal data and a measured bioelectrical impedance, and a display unit for displaying the calculated data related to the body composition. Thereby, a user can acquire data related to his/her own body composition by use of this bioelectrical impedance measuring device.

DETAILED DESCRIPTION OF THE PREFERRED EMBODIMENTS

Hereinafter, an embodiment of the present invention will be described with reference to the drawings.

Figure 1:
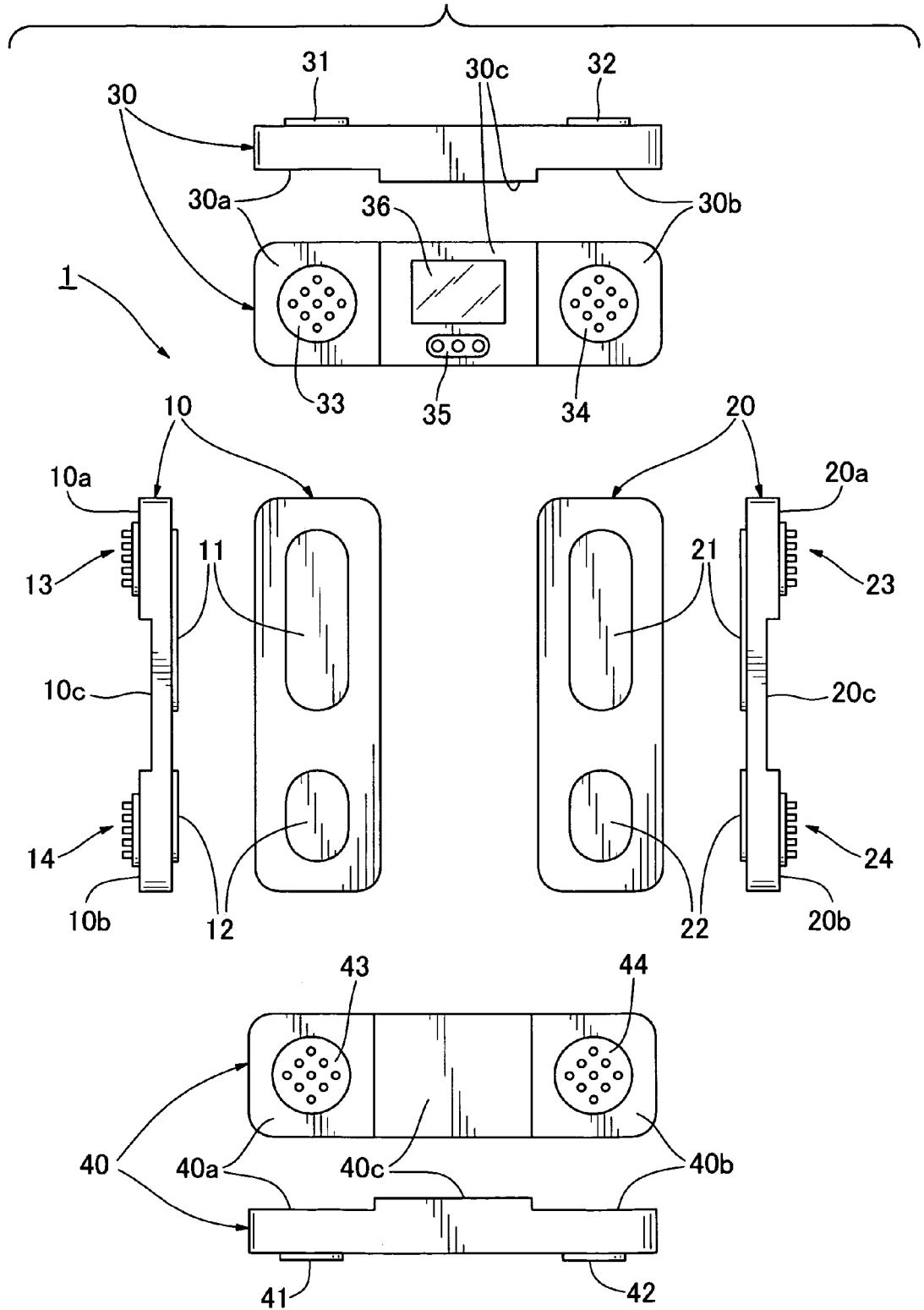
FIG. 1 is an external view of a bioelectrical impedance measuring device in a disassembled state as one embodiment of the present invention.
Figure 2:
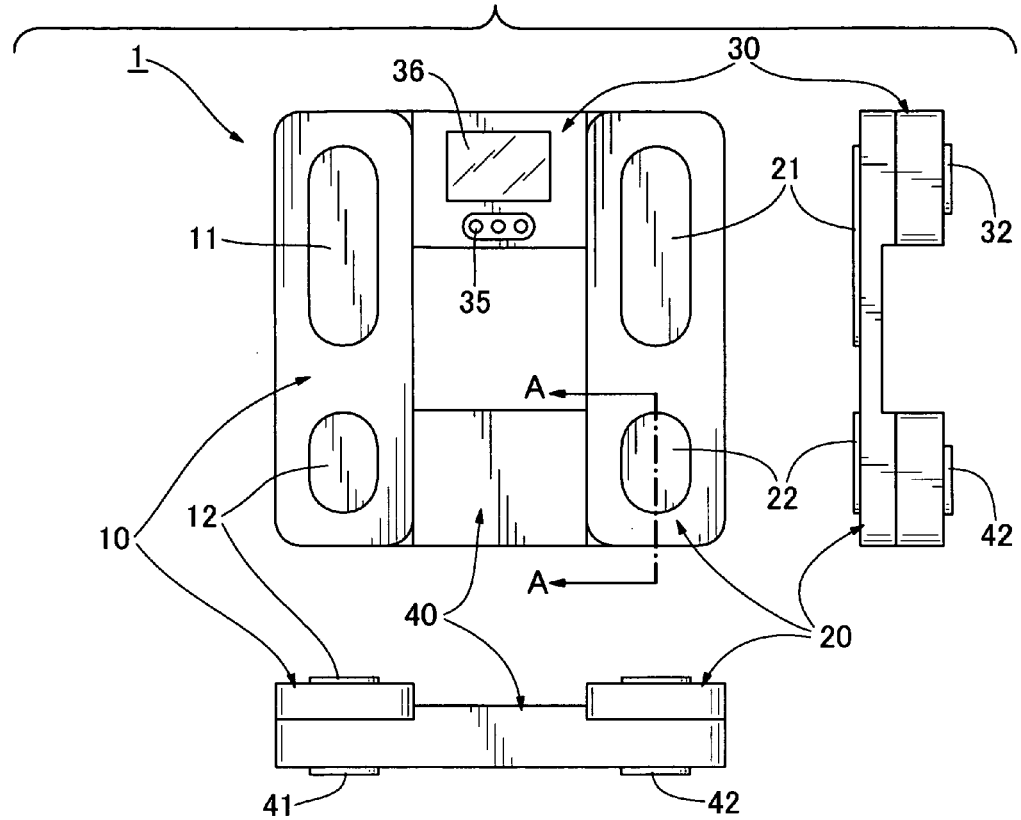
FIG. 2 is an external view of the bioelectrical impedance measuring device in an assembled state as one embodiment of the present invention.

FIGS. 1 and 2 show external views of a bioelectrical impedance measuring device 1 according to the present invention. FIG. 1 shows top views and side views of the device 1 in a disassembled state, and FIG. 2 shows a top view and side views of the device 1 in an assembled state. As in the case of a conventional bioelectrical impedance measuring device as described in the foregoing patent publication 1, this bioelectrical impedance measuring device 1 not only measures the body weight and bioelectrical impedance of a user but also calculate data related to body composition such as a body fat percentage (mass) based on personal data such as a body height which has been entered by the user and the measured body weight and bioelectrical impedance and display the calculated data.

As shown in FIG. 1, this bioelectrical impedance measuring device 1 comprises a first electrode unit 10, a second electrode unit 20, a control circuit unit 30, and an auxiliary unit 40.

The first electrode unit 10 is formed in a nearly rectangular shape when viewed from above. On the top surface thereof, electrodes 11 and 12 for measuring a bioelectrical impedance are provided. Further, the first electrode unit 10 has steps between the undersurface 10c of the middle portion and the undersurface 10a of one end in a longitudinal direction and the undersurface 10b of the other end in the longitudinal direction. Thus, the first electrode unit 10 is formed in a nearly concave shape when viewed from a longer side thereof. Further, a connection terminal 13 is provided on the undersurface 10a of one end in the longitudinal direction, and a connection terminal 14 is provided on the undersurface 10b of the other end in the longitudinal direction.

The second electrode unit 20 has the same shape and constitution as those of the first electrode unit. On the top surface thereof, electrodes 21 and 22 for measuring a bioelectrical impedance are provided. A connection terminal 23 is provided on the under surface 20a of one end in a longitudinal direction, and a connection terminal 24 is provided on the undersurface 20b of the other end in the longitudinal direction.

The control circuit unit 30 is formed in a rectangular shape similar to those of the first electrode unit and second electrode unit when viewed from above. Further, the control circuit unit 30 has steps between the top surface 30c of the middle portion and the top surface 30a of one end in a longitudinal direction and the top surface 30b of the other end in the longitudinal direction. Thus, the control circuit unit 30 is formed in a nearly convex shape when viewed from a longer side thereof. Further, a connection terminal 33 is provided on the top surface 30a of one end in the longitudinal direction, and a connection terminal 34 is provided on the top surface 30b of the other end in the longitudinal direction. In addition, a load sensor 31 for measuring a body weight is embedded in the undersurface of one end in the longitudinal direction, and a load sensor 32 is embedded in the undersurface of the other end in the longitudinal direction. Further, on the top surface 30c of the middle portion, an input unit 35 which is used by a user to enter personal data such as a body height and a display unit 36 for displaying data related to body composition such as a body fat percentage (mass) which is calculated by the bioelectrical impedance measuring device are provided. Further, in the control circuit unit 30, an electric control circuit 37 for measuring the bioelectrical impedance of a user via the electrodes 11, 12, 21 and 22 of the first and second electrode units is incorporated (refer to FIG. 5). In this electric control circuit 37, an arithmetic unit 37a for calculating data related to body composition such as a body fat percentage (mass) is incorporated.

The auxiliary unit 40 has an appearance similar to that of the control circuit unit 30. A connection terminal 43 is provided on the top surface 40a of one end in a longitudinal direction of the unit 40, and a connection terminal 44 is provided on the top surface 40b of the other end in the longitudinal direction. In addition, a load sensor 41 for measuring a body weight is embedded in the undersurface of one end in the longitudinal direction, and a load sensor 42 is embedded in the undersurface of the other end in the longitudinal direction.

Then, the undersurface 10a of the first electrode unit 10 is directly placed on the top surface 30a of the control circuit unit 30, the under surface 10b is directly placed on the top surface 40a of the auxiliary unit 40, the undersurface 20a of the second electrode unit 20 is directly placed on the top surface 30b of the control circuit unit 30 and the undersurface 20b is directly placed on the top surface 40b of the auxiliary unit 40 so as to detachably connect the connection terminal 13 to the connection terminal 33, the connection terminal 14 to the connection terminal 43, the connection terminal 23 to the connection terminal 34 and the connection terminal 24 to the connection terminal 44. As a result, the bioelectrical impedance measuring device 1 which is in the form of hollow square when viewed from above as shown in FIG. 2 is formed.

Figure 3:
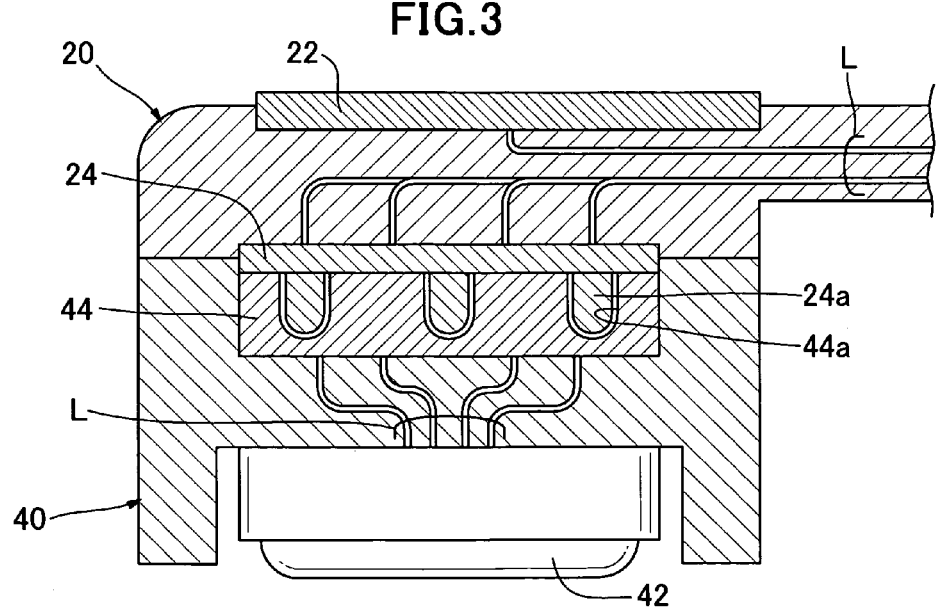
FIG. 3 is a cross sectional view on A—A in FIG. 2.

FIG. 3 is a cross sectional view on A—A in FIG. 2. The connection terminal 24 of the second electrode unit 20 is a male terminal having a plurality of connection pins 24a, and the connection terminal 44 of the auxiliary unit 40 is a female terminal having a plurality of connection holes 44a. As shown in FIG. 3, the connection pins 24a are inserted in the connection holes 44a so as to connect the connection terminal 24 to the connection terminal 44 in a detachable manner. In FIG. 3, the connection terminal 24 and the connection terminal 44 are drawn not in contact with each other for the sake of convenience; in reality, however, they are electrically connected to each other so as to pass electricity. Further, the connection terminal 44 is connected to the load sensor 42 (a known load cell comprising a strain gauge can be used as the sensor 42) via an electric wire L, and the connection terminal 24 and the electrode 22 are connected to the connection terminal 23 which is not shown via electric wires L.

Figure 4A:
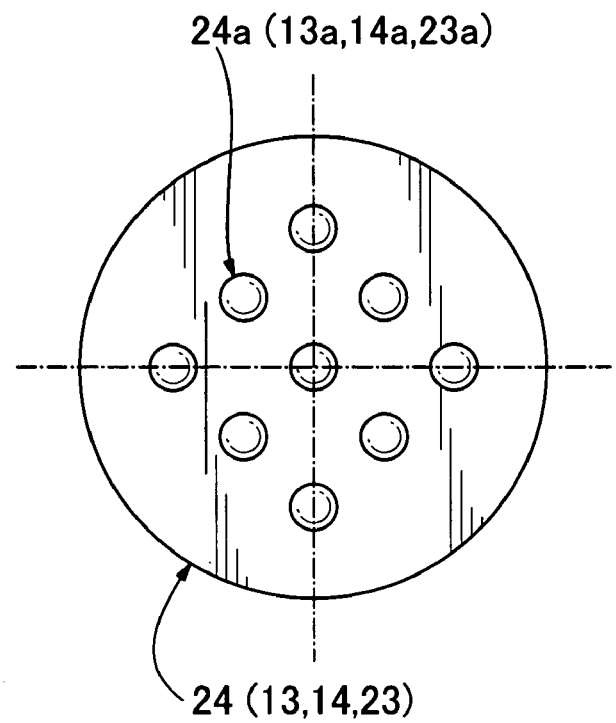
FIGS. 4A and 4B are diagrams showing connection terminals of the bioelectrical impedance measuring device as one embodiment of the present invention.
Figure 4B:
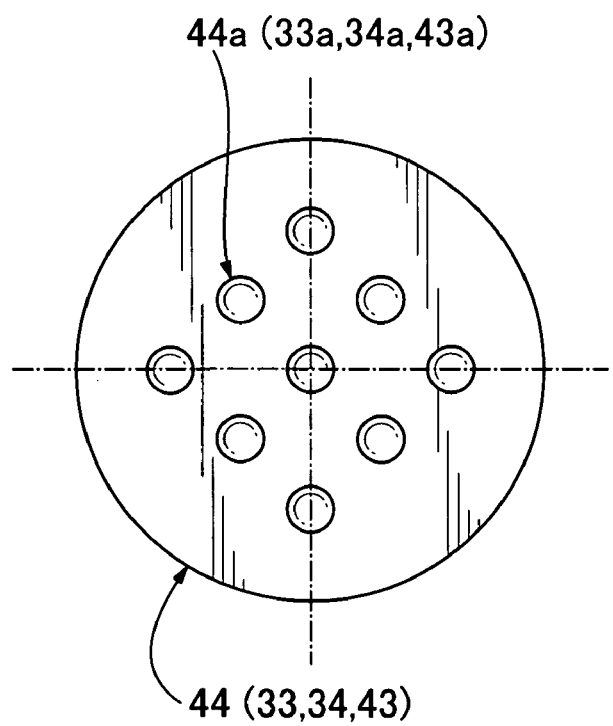

FIG. 4A shows an enlarged view of the connection terminal 24, and FIG. 4B shows an enlarged view of the connection terminal 44. As shown in these drawings, the connection pins 24a and the connection holes 44a are preferably positioned symmetrically in vertical and horizontal directions. When a plurality of connection terminals are positioned symmetrically in vertical and horizontal directions, the units can be stacked stably and detachably via the connection terminals as will be described later. It is also acceptable that the connection terminal 24 is female and the connection terminal 44 is male. Further, the connection terminals 13, 14 and 23 have the same constitution as that of the connection terminal 24, and the connection terminals 33, 34 and 43 have the same constitution as that of the connection terminal 44.

Figure 5:
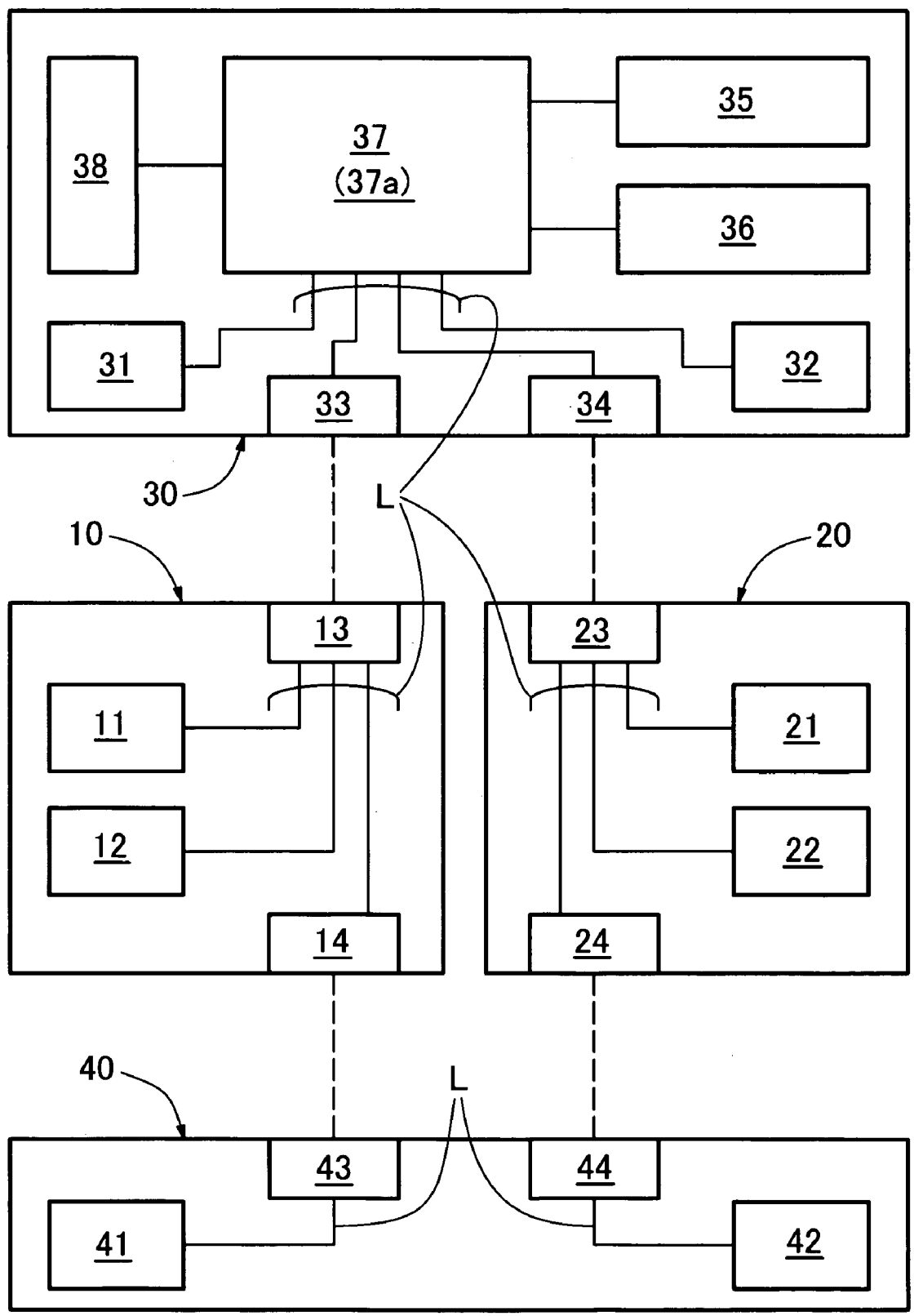
FIG. 5 is a schematic diagram illustrating an internal electrical connection relationship in the bioelectrical impedance measuring device as one embodiment of the present invention.

FIG. 5 is a schematic diagram illustrating an internal electrical connection relationship in each unit. In the first electrode unit 10, the electrodes 11 and 12 are connected to the connection terminal 13 via electric wires L, and the connection terminal 13 is also connected to the connection terminal 14 via an electric wire L. In the second electrode unit 20 as well, the electrodes 21 and 22 and the connection terminal 24 are connected to the connection terminal 23 via electric wires L. In the control circuit unit 30, the load sensors 31 and 32, the connection terminals 33 and 34, the input unit 35 and the display unit 36 are connected to the electric control circuit 37 via electric wires L. Further, a power source 38 such as a battery is also incorporated in the control circuit unit 30, and the power source 38 is also connected to the electric control circuit 37. In the auxiliary unit, the load sensor 41 is connected to the connection terminal 43 via an electric wire L, and the load sensor 42 is connected to the connection terminal 44 via an electric wire L.

In the bioelectrical impedance measuring device in which the units are assembled in the form of hollow square when viewed from above as shown in FIG. 2 and the constituents are electrically connected as shown in FIG. 5, when a user enters personal data such as a body height by operating the input unit 35 and stands on the top surfaces of the electrode units 10 and 20 with the bottoms of both feet in contact with the electrodes 13, 14, 23 and 24, detection signals of the load sensors 31, 32, 41 and 42 are sent to the electric control circuit 37 via the electric wires and the connection terminals so as to measure the body weight of the user. Further, an alternating current is fed from the electric control circuit 37 to between both feet of the user via the electric wires, the connection terminals and the electrodes 11 and 21, and a potential difference (voltage) between both feet at that time is sent to the electric control circuit 37 from the electrodes 12 and 22 via the electric wires and the connection terminals so as to measure the bioelectrical impedance of the user. Then, in the arithmetic unit 37a incorporated in the electric control circuit 37, data related to body composition such as a body fat percentage (mass) is calculated based on the entered personal data and the measured body weight and bioelectrical impedance and displayed on the display unit 36. The data related to body composition include a variety of data which can be calculated by use of a bioelectrical impedance, such as an internal fat mass, a body water percentage (content), a muscle percentage (mass), a bone mass and a basal metabolic rate.

Figure 6:
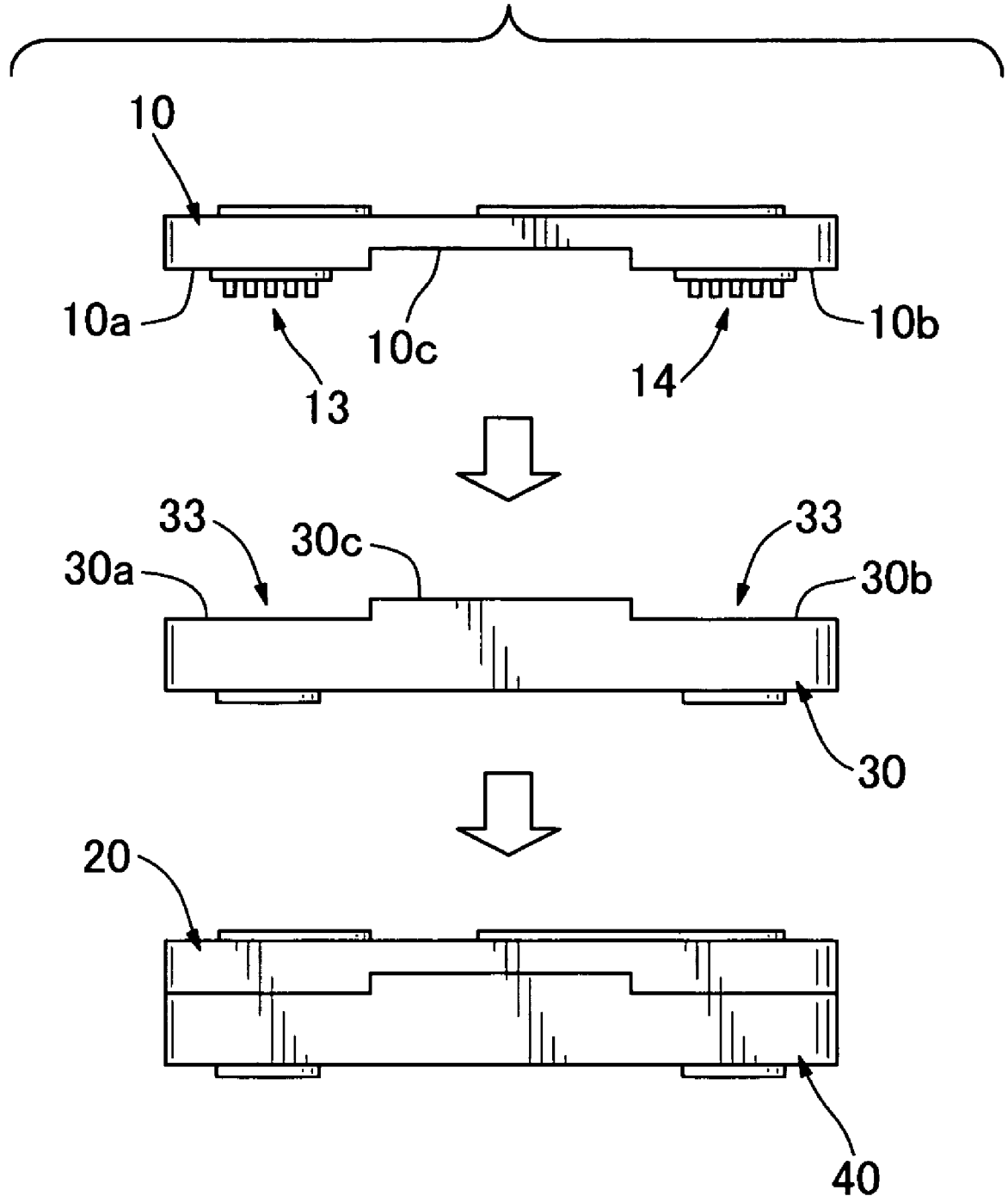
FIG. 6 is a side view of the bioelectrical impedance measuring device as one embodiment of the present invention when it is disassembled and stacked.

FIG. 6 is a side view of the bioelectrical impedance measuring device 1 when disassembled and stacked so as to be carried around or stored. As shown in FIG. 6, when the first electrode unit 10 and the second electrode unit 20 which are formed in a nearly concave shape when viewed from a side thereof are stacked on the control circuit unit 30 and the auxiliary unit 40 which are formed in a nearly convex shape when viewed from a side thereof, respectively, by fitting their concave and convex portions appropriately in their longitudinal directions, the units can be stacked stably with a minimum overall height. More specifically, for example, when the first electrode unit 10 is stacked on the control circuit unit 30, the undersurfaces 10a, 10b and 10c of the first electrode unit 10 are placed on the top surfaces 30a, 30b and 30c of the control circuit unit 30, respectively. Further, since the connection terminal shave connection pins or connection holes formed thereon symmetrically in vertical and horizontal directions as described above, the connection terminal 13 and the connection terminal 14 can be detachably attached to the connection terminal 33 and the connection terminal 34, respectively, in this case as well, thereby achieving stabilization of the stacked units.

Figure 7A:
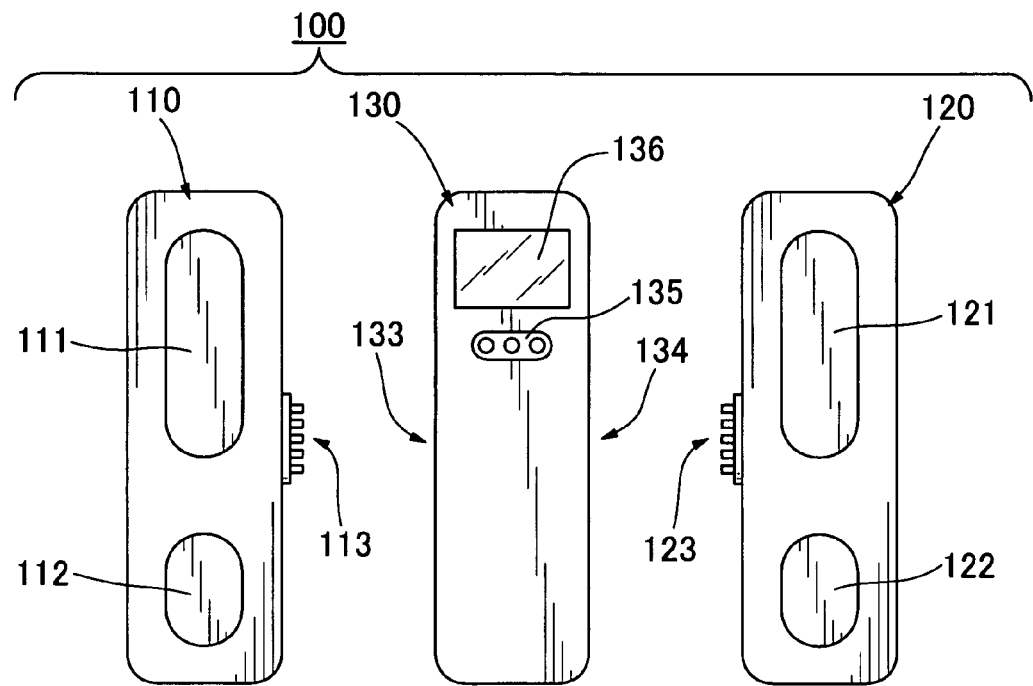
FIGS. 7A and 7B are a top view and side view of the appearance of a bioelectrical impedance measuring device as another embodiment of the present invention, respectively.
Figure 7B:
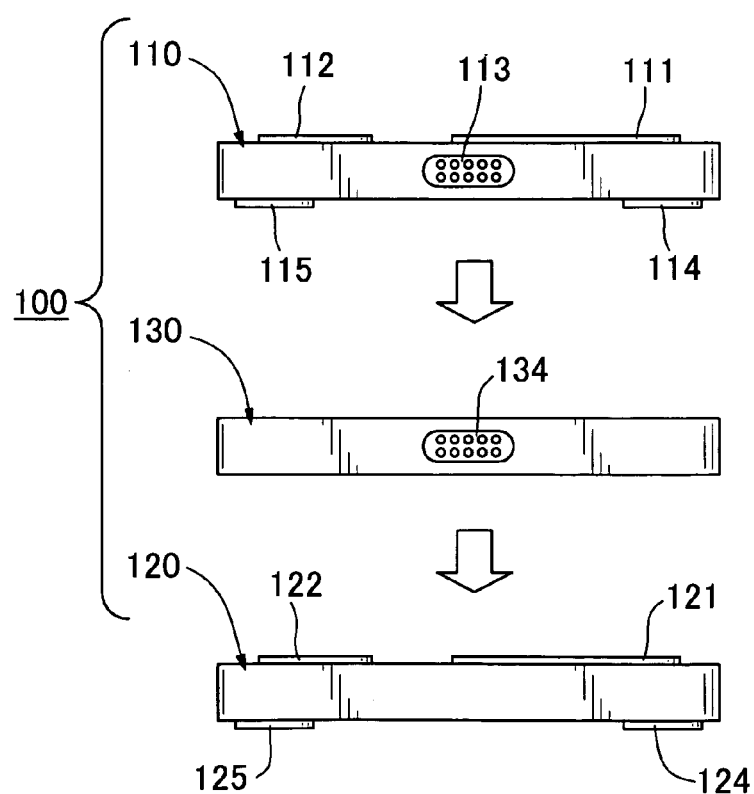

FIG. 7 shows external views of a bioelectrical impedance measuring device 100 as another embodiment of the present invention. FIG. 7A shows a top view thereof, and FIG. 7B shows a side view thereof.

As shown in FIG. 7A, the bioelectrical impedance measuring device 100 comprises a first electrode unit 110, a second electrode unit 120 and a control circuit unit 130 which are formed in a nearly rectangular shape when viewed from above.

On the top surfaces of the first electrode unit 110 and the second electrode unit 120, a left-toe-side electrode 111 and a left-heel-side electrode 112 and a right-toe-side electrode 121 and a right-heel-side electrode 122 are provided, respectively, so as to measure a bioelectrical impedance. Further, on longer sides of the unit 110 and the unit 120, connection terminals 113 and 123 are provided, and on the undersurfaces of the unit 110 and the unit 120, load sensors 114 and 115 and load sensors 124 and 125 are provided, respectively (refer to FIG. 7B). The control circuit unit 130 has an input unit 135 and a display unit 136 provided on the top surface thereof, and on both longer sides of the unit 130, connection terminals 133 and 134 are provided. Further, inside the unit 130, an electric control circuit (not shown) for measuring a bioelectrical impedance is incorporated. In the present embodiment as well, an arithmetic unit for calculating data related to body composition is incorporated in this electric control circuit.

Further, via internal electric wires (not shown), the electrodes 111 and 112 and the load sensors 114 and 115 are connected to the connection terminal 113, the electrodes 121 and 122 and the load sensors 124 and 125 are connected to the connection terminal 123, and the connection terminals 133 and 134, the input unit 135 and the display unit 136 are connected to the electric control circuit. The connection terminals 113 and 123 are detachably connected to the connection terminals 133 and 134, respectively. As a result, the bioelectrical impedance measuring device 100 is obtained in an assembled state. Descriptions about measurement of bioelectrical impedance and calculation of data related to body composition by the bioelectrical impedance measuring device 100 will be omitted since they are carried out in the same manner as in the bioelectrical impedance measuring device 1 which is shown in FIGS. 1 to 6.

FIG. 7B is a side view of the bioelectrical impedance measuring device 100 when disassembled and stacked so as to be carried around or stored. As shown in FIG. 7B, the first electrode unit, the second electrode unit and the control circuit unit are stacked with their longer sides aligned with each other, thereby making the bioelectrical impedance measuring device 100 easy to carry or store.

Modes for carrying out the present invention are not limited to the embodiments described above by use of the drawings. To say nothing of the variations and applications described along with the embodiments, various variations and applications are possible without deviating from the constitutions described in the claims.

For example, in the bioelectrical impedance measuring device 1 which is shown in FIGS. 1 to 6, the sizes and shapes of the units can be changed individually. For example, it is possible that the control circuit unit 30 is formed slightly larger in a width direction than the auxiliary unit 40 and the input unit 35 and display unit 36 of large size are installed so as to improve the operability of the device 1 to users.

Further, it is also possible to make the input unit 35 (135) and the display unit 36 (136) of the bioelectrical impedance measuring device 1 (100) detachable from the control circuit unit 30 (130) together with the arithmetic unit 37a and the like and have them communicate with one another by use of infrared light.

Further, such a constitution is also acceptable that the load sensors for measuring a body weight are omitted and a user enters his/her own body weight by means of the input unit 35 (135) as required.

In addition, for both the bioelectrical impedance measuring device 1 which is shown in FIGS. 1 to 6 and the bioelectrical impedance measuring device 100 which is shown in FIG. 7, it is possible to prepare a variety of units which are different in design, color or mode of displaying data (e.g., merely in numeric values or as a graph) to the display unit and have a user select each unit according to his preference and application.

A bioelectrical impedance measuring device of the present invention comprises a first electrode unit and a second electrode unit which are nearly rectangular in shape and have electrodes for measuring a bioelectrical impedance on the top surfaces thereof, and a control circuit unit which incorporates an electric control circuit for measuring a bioelectrical impedance and is detachably attached to the first electrode unit and the second electrode unit via connection terminals. Accordingly, a user can disassemble the device into the control circuit unit, the first electrode unit and the second electrode unit and stack these units and can therefore carry around or store the device easily.

Further, the bioelectrical impedance measuring device of the present invention which further comprises an auxiliary unit may be constituted such that one end of the first electrode unit and one end of the second electrode unit are placed on the top surfaces of the ends of the control circuit unit and the other end of the first electrode unit and the other end of the second electrode unit are placed on the top surfaces of the ends of the auxiliary unit, whereby the control circuit unit, the first electrode unit, the second electrode unit and the auxiliary unit are detachably assembled via connection terminals. In that case, since the device in an assembled state is in the form of hollow square when viewed from above, the assembled device shows good strength and rigidity.

Further, in the bioelectrical impedance measuring device of the present invention, the first electrode unit and the second electrode unit may be formed in a nearly concave shape when viewed from a longer side thereof, and the control circuit unit and the auxiliary unit may be formed in a nearly convex shape when viewed from a longer side thereof. In that case, the control circuit unit and the auxiliary unit and the first electrode unit and the second electrode unit can be stacked stably by fitting their concave and convex portions with a minimum overall height, thereby further facilitating carrying and storing of the device.

Further, in the bioelectrical impedance measuring device of the present invention, the control circuit unit and the auxiliary unit may incorporate load sensors for measuring a body weight. In that case, when a user stands on the top surfaces of the first electrode unit and the second electrode unit of the device in an assembled state, the body weight of the user is passed down to the control circuit unit and the auxiliary unit on which the first electrode unit and the second electrode unit are placed and can be measured by the load sensors.

Further, in the bioelectrical impedance measuring device of the present invention, the control circuit unit may further incorporate an input unit used by a user to enter personal data, an arithmetic unit for calculating data related to the body composition of the user based on at least the personal data and a measured bioelectrical impedance, and a display unit for displaying the calculated data related to the body composition. In that case, a user can acquire data related to his own body composition by use of this bioelectrical impedance measuring device.

What is claimed is:

1. A bioelectrical impedance measuring device comprising: a first electrode unit and a second electrode unit which are nearly rectangular in shape and have electrodes for measuring a bioelectrical impedance on the top surfaces thereof, a control circuit unit which incorporates an electric control circuit for measuring a bioelectrical impedance and is detachably attached to the first electrode unit and the second electrode unit via connection terminals, and an auxiliary unit, wherein one end of the first electrode unit and one end of the second electrode unit are placed on the top surfaces of the ends of the control circuit unit and the other end of the first electrode unit and the other end of the second electrode unit are placed on the top surfaces of the ends of the auxiliary unit, whereby the control circuit unit, the first electrode unit, the second electrode unit and the auxiliary unit are detachably assembled via connection terminals.

2. The device of claim 1, wherein the first electrode unit and the second electrode unit are formed in a nearly concave shape when viewed from a longer side thereof, and the control circuit unit and the auxiliary unit are formed in a nearly convex shape when viewed from a longer side thereof.

3. The device of claim 1 or 2, wherein the control circuit unit and the auxiliary unit incorporate load sensors for measuring a body weight.

4. The device of claim 1 or 2, wherein the control circuit unit further incorporates:
   an input unit operable by a user to enter personal data,
   an arithmetic unit for calculating data related to the body composition of the user based on at least the personal data and a measured bioelectrical impedance, and
   a display unit for displaying the calculated data related to the body composition.

5. The device of claim 3, wherein the control circuit unit further comprises:
   an input unit operable by a user to enter personal data,
   an arithmetic unit for calculating data related to the body composition of the user based on at least the personal data and a measured bioelectrical impedance, and
   a display unit for displaying the calculated data related to the body composition.

* * * * *